United States Patent [19]

Klingler et al.

[11] 4,226,803

[45] Oct. 7, 1980

[54] PROCESS FOR PRODUCTION OF OPTICALLY ACTIVE BASES

[75] Inventors: Karl H. Klingler, Langen; Horst Traube, Dreieich, both of Fed. Rep. of Germany

[73] Assignee: Deutsche Gold- und Silber-Scheideanstalt vormals Roessler, Frankfurt, Fed. Rep. of Germany

[21] Appl. No.: 969,067

[22] Filed: Dec. 13, 1978

[30] Foreign Application Priority Data

Dec. 16, 1977 [GB] United Kingdom ............... 52421/77

[51] Int. Cl.$^2$ ................... C07C 101/04; C07B 19/00; C07C 91/16; C07C 87/28
[52] U.S. Cl. .................. 260/501.11; 260/340.5 R; 260/570.5 R; 260/570.6; 562/401
[58] Field of Search ............... 562/401, 444; 260/570.5 R, 570.6, 340.5 R, 501.11

[56] References Cited

U.S. PATENT DOCUMENTS

| 2,276,508 | 3/1942 | Nabenhauer | 260/501.11 |
| 3,028,395 | 4/1962 | Gillingham | 260/501.11 |
| 3,028,430 | 4/1962 | Gillingham | 260/501.11 |
| 3,576,854 | 4/1971 | Felder et al. | 562/401 |
| 4,002,666 | 1/1977 | Shirai et al. | 260/501.11 |

FOREIGN PATENT DOCUMENTS 2558507 9/1976 Fed. Rep. of Germany .
901438 7/1962 United Kingdom .
1137596 12/1968 United Kingdom .

OTHER PUBLICATIONS

Helvetica Chemica Acta, vol. 52, Nr 36-37, pp. 329-333, (1969).

*Primary Examiner*—Natalie Trousof
*Assistant Examiner*—Vera C. Clarke
*Attorney, Agent, or Firm*—Cushman, Darby & Cushman

[57] ABSTRACT

Optically active bases are prepared by reacting the racemic base with an optically active half amide of an unsaturated aliphatic dicarboxylic acid of the formula

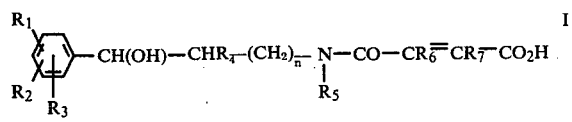

where $R_1$, $R_2$ and $R_3$ are the same of different and are hydrogen, halogen, a hydroxy group, a methyl group or a methoxy group or two of $R_1$, $R_2$ and $R_3$ together are a methylenedioxy group, $R_4$ is hydrogen or a methyl group, $R_5$, $R_6$ and $R_7$ independently are hydrogen or a $C_1$–$C_4$ alkyl group and n is 0 or 1 and optionally splitting an optically homogeneous salt fraction into the corresponding optically active base and the added half amide.

27 Claims, No Drawings

PROCESS FOR PRODUCTION OF OPTICALLY ACTIVE BASES

BACKGROUND OF THE INVENTION

In Helvetica Chemica Acta Vol. 52, pages 329=333 (1969) and Felder U.S. Pat. No. 3,576,854 there is described the optical splitting of (R) (S)-(1-phenylethyl)-amine, (R) (S)-2-aminobutanol-(1) and 1-(R) (S)-threo-1-(4-nitrophenyl)-2-aminopropanediol-(1,3) using N-[(R)-(1-phenylethyl)]- or N-[(S)-(1-phenylethyl)]-succinic acid monoamide and for splitting of (R) (S)-1-phenyl-2-aminopropane using N-[(R) or (S)-(1-phenylethyl)]-phthalic acid monoamide.

Furthermore it is known to separate racemic norephedrine into the right and left light rotating forms with optically active pantolactone (German Offenlegungsschrift 2,558,507).

However, in the known processes the yields of the pure optically active forms are unsatisfactory; also, frequently the purity of the product of the process is insufficient.

SUMMARY OF THE INVENTION

According to the invention optically active bases are prepared by reacting the racemic base with an optically active half amide of an unsaturated aliphatic dicarboxylic acid of the formula

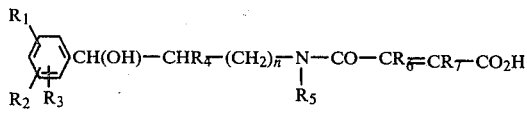

where $R_1$, $R_2$ and $R_3$ are the same or different and are hydrogen, halogen, a hydroxy group, a methyl group or a methoxy group or two of $R_1$, $R_2$ and $R_3$ together are a methylenedioxy group, $R_4$ is hydrogen or a methyl group, $R_5$, $R_6$ and $R_7$ independently are hydrogen or a $C_1$–$C_4$ alkyl group and n is 0 or 1 and optionally splitting an optically homogeneous salt fraction into the corresponding optically active base and the added half amide.

In the case where the groups $R_1$, $R_2$ and $R_3$ are halogen atoms they are fluorine, chlorine or bromine. In case the groups $R_5$, $R_6$ and $R_7$ are alkyl groups they are preferably methyl or ethyl groups.

In addition to the specific monoamides employed in the working examples illustrative of other monoamides which can be used in the invention include (−)-ψ-N-(1-methyl-2-phenyl-2-hydroxyethyl)-methyl maleic acid monoamide, (−)-N-(1-methyl-2-p-hydroxyphenyl-2-hydroxyethyl)-maleic acid monoamide, (−) N-[2-(3-hydroxyphenyl)-2-hydroxyethyl]-maleic acid monoamide, (+)-N-[2-(3-hydroxyphenyl)-2-hydroxyethyl]-maleic acid monoamide, (−)-N-[2-(3-hydroxyphenyl)-2-hydroxyethyl]-maleic acid as well as the (+) or (−) optically active forms of the following monoamides amidoacids are N-(3-phenyl-3-hydroxyethyl)maleic acid monoamide, (−)-ψ-N-(1-methyl-2-phenyl-2-hydroxyethyl)-methyl-maleic acid monoamide, N-(2-phenyl-2-hydroxyethyl) maleic acid monoamide, N-(3-p-chlorophenyl-3-hydroxypropyl) maleic acid monoamide, N-(1-methyl-2-p-chlorophenyl-2-hydroxyethyl) maleic acid monoamide, N-(1-methyl-2-o-chlorophenyl-2-hydroxyethyl) maleic acid monoamide, N-(1-methyl-2-m-chlorophenyl-2-hydroxyethyl) maleic acid monoamide, N-(1-methyl-2-p-bromophenyl-2-hydroxyethyl) maleic acid monoamide, N-(1-methyl-2-p-fluorophenyl-2-hydroxyethyl) maleic acid monoamide, N-(1-methyl-2-o,p-dichlorophenyl-2-hydroxyethyl) maleic acid monoamide, N-(1-methyl-2-p-methylphenyl-2-hydroxyethyl maleic acid monoamide, N-(2-p-methylphenyl-2-hydroxyethyl) maleic acid monoamice, N-(1-methyl-2-o-methylphenyl-2-hydroxyethyl) maleic acid monoamide, N-(1-methyl-2-m-methylphenyl-2-hydroxyethyl) maleic acid monoamide, N-(1-methyl-2-o.p=dimethylphenyl-2-hydroxyethyl) maleic acid monoamide, N-(1-methyl-2-2′,4′,6′-trimethylphenyl-2-hydroxyethyl) maleic acid monoamide, N-(1-methyl-2-p-methoxyphenyl)-2-hydroxyethyl) maleic acid monoamide, N-)2-o-methoxyphenyl)-2-hydroxyethyl) maleic acid monoamide, N-(1-methyl-2′,3′-methylenedioxyphenyl)-2-hydroxyethyl) maleic acid monoamide, N-(1-methyl-3′,4′-methylenedioxyphenyl)-2-hydroxyethyl) maleic acid monoamide, N-methyl-N-(1-methyl-2-phenyl-2-hydroxyethyl) maleic acid monoamide, N-(1-methyl-2-o,p-dihydroxyphenyl-2-hydroxyethyl) maleic acid monoamide, N-(1-methyl-2-phenyl-2-hydroxyethyl) ethyl maleic acid monoamide, N-(1-methyl-2-phenyl-2-hydroxyethyl) butyl maleic acid monoamide, N-(1-methyl-2-phenyl-2-hydroxyethyl) dimethyl maleic acid monoamide, N-(1-methyl-2-phenyl-2-hydroxyethyl) diethyl maleic acid monoamide, N-(2-methyl-3-phenyl-3-hydroxypropyl) maleic acid monoamide.

The half amides employed in the invention can be prepared as disclosed in companion Klingler, et al application Ser. No. 969,068 filed on even date and entitled "NEW MALEIC ACID HALFAMIDES" (based on British application 52422/77). The entire disclosure of the copending Klingler, et al application is hereby incorporated by reference and relied upon. Likewise they can be prepared by the processes of British Pat. No. 901,438 or British Pat. No. 1,137,596 by reacting maleic anhydride with the appropriate, optically active base.

As racemic bases which can be resolved by the optically active monoamides there can be mentioned, norephedrine, pseudonorephedrine, ephedrine, amphetamine, p-methylnorephedrine, o,p or m-hydroxynorephedrine, (i.e., 2-amino-1-(2′ or 4′ or 3′-hydroxy) phenyl-1-propanol), 3,4-dihydroxy or 3,5-dihydroxy norephedrine (i.e. 2-amino-1-(3′,4′-dihydroxy) phenyl-1-propanol or 2-amino-1-(3′,5′-dihydroxy) phenyl-1-propanol), 2-amino-1-hydroxy-1-phenyl-butane,2-amino-1-(4′-chloro)-hexyl-1-propanol, 2-amino-1(2′-chloro) phenyl-1-propanol, 2-amino-1-p-tolyl-1-propanol, phenoxypropanol-2-amine, p-methoxynorephedrine, p-fluoronorephedrine, 3,4-methylenedioxynorephedrine, α-naphthoxypropanol-2-amine, o-allyloxyphenoxypropanol-2-amine, atropine, codeine, noradrenaline, adrenaline, 3,4-dihydroxyephedrine.

The process of the invention permits the obtaining of optically active physiologically effective amines in a simple manner with the requisite purity.

For the splitting (i.e. resolution) of the racemate there can be reacted either equivalent or non equivalent amounts of amidoacid (0.4 to 1.2 moles preferably 0.5 to 1.0 moles of amidoacid per mole of base) and base in a solvent at a temperature between 0°–100° C., for example 10°–40° C., preferably 15°–30° C. The reaction can take place with or without stirring. In a given case slow cooling during the crystallization is suitable. Innoculation with the desired diastereoisomer salt previously produced from pure components is recommended. As in other processes for splitting racemates the solvent or mixture of solvents can be varied in a wide range. For example as solvents there can be used alcohols such as methanol, ethanol, isopropanol, propanol and butanol; ketones such as acetone, methyl ethyl ketone and methyl isobutyl ketone; esters such as ethyl acetate and butyl acetate, amides such as dimethyl formamide and dimethyl acetamide; ethers such as diethyl ether and dioxane; water, particularly admixed with an organic solvent. The amount of solvent based on the sum of the amounts of acid and base added is generally two to twenty fold; the preferred range is between about three to eight fold.

The amines for the reaction with the amidoacid can be added also as corresponding salts with acids, preferably weak acids (for example the acetate). In a given case in such a case the amidoacid can also be added as a metal salt (for example alkali metal salts, e.g. sodium or potassium salts).

There are especially employed in the process of the invention half amides of the general formula

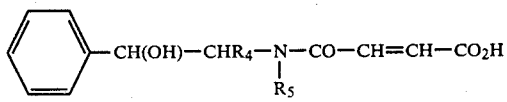

II wherein $R_4$ is hydrogen or a methyl group and $R_5$ is hydrogen or a $C_1$-$C_4$ alkyl group, for example a methyl, ethyl, propyl, butyl or isobutyl group. Both $R_4$ and $R_5$ can be hydrogen. Preferably there are used half amides of formula II where in $R_4$ is a methyl group and $R_5$ is hydrogen, for example the maleic acid halfamides of (+)-pseduonorephedrine of (−)-pseudonorephedrine.

If the amine components of the halfamides of formula I or of formula II contain several asymmetric centers, as for example is the case of norephedrine as well as norephedrine derivatives which are substituted in the phenyl nucleus, it is frequently advantageously before the production of the halfamide to change the configuration of one asymmetrical center of the basic component in known manner for this purpose. Particularly this is the case in the rearrangement of (+)-norephedrine into (−)-ψ-norephedrine (−)-pseudonorephedrine) or of (−)-norephedrine into (+)-ψ-norephedrine (+)-pseudonorephedrine). The analogy is valid for (+) or (−)-norephedrine which is substituted in the phenyl nucleus by the groups $R_1$, $R_2$ and $R_3$ according to formula I. These pseudo forms are particularly suited for the racemate splitting.

The previously mentioned rearrangement of optically active norephedrine into the in turn oppositely light rotating pseudonorephedrine is described in the literature: The OH group of the norephedrine is replaced by chlorine by means of $SOCl_2$ or HCl and subsequently saponified in the reaction mixture by boiling with water again to the OH group (Walden inversion). Also before the chlorination the amino group can be protected by acylation (e.g. acetylation) and subsequently the acyl group split off in customary manner by hydrolysis or hydrogenolysis. Norephedrine derivatives which are substituted in the phenyl nucleus by $R_1$, $R_2$ and $R_3$ act in a completely analogous manner.

As a rule in the process of the invention after the reaction of the halfamide I with the base one pure diastereomeric form precipitates out while the other remains in solution. However, in the case in which one or the other diastereomeric form precipitates greatly contaminated with the other then the purification takes place in the customary manner for this through fractional crystallization.

The diastereomers obtained according to the process of the invention decomposed in a simple manner using alkali (for example alkali metal hydroxides such as sodium or potassium hydroxide), ammonia or a mineral acid such as hydrochloric acid of sulfuric acid. The more difficulty soluble diastereomer is treated for example with the alkali (preferably $NH_3$ or NaOH) and, in case the base does not precipitate, extracted with a water incompatible or immiscible solvent such as chloroform, methylene chloride, benzene or ether, whereby the optically active form can be isolated in greater purity from the organic phase. The mother liquor, from which the more difficulty soluble diastereomer was separated, is generally distilled off and the residue taken up in a solvent in which the residual (±) base separates out as insoluble (for example aromatic hydrocarbons such as toluene, xylene or benzene). After several hours the (±) base is separated off and the filtrate evaporated whereby the other antipode of the base remains behind.

The aqueous phase from which the optically active base is extracted is then acidified with a mineral acid (HCl or $H_2SO_4$), whereby the amidoacid precipitates out. The thus recovered amidoacids for most part can again be added for the racemate splitting without further purification.

If the salts obtained in the splitting of the racemate are split up with acids (mineral acids such as HCl, $H_2SO_4$) then the amidoacid precipitates out first. The filtrate is either directly or after concentration made alkaline and the optically active base extracted by a solvent (lower aliphatic halohydrocarbons such as chloroform or lower aliphatic dialkyl ethers such as diethyl ether).

As racemic bases which can be split by the process there are particularly suited amines of the formula

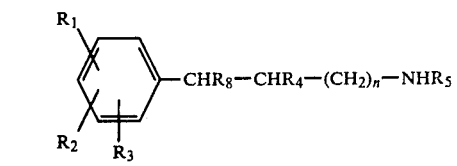

III where $R_1$, $R_2$ and $R_3$ are the same or different and are hydrogen, a halogen atom (e.g. fluorine, chlorine or bromine), a hydroxy group, a methyl group or a methoxy group or two of $R_1$, $R_2$ and $R_3$ together are a methylenedioxy group, $R_4$ is hydrogen or a methyl group, $R_5$ is hydrogen or a $C_1$-$C_4$ alkyl group, e.g. methyl, ethyl, propyl, isopropyl or butyl, $R_8$ is hydrogen or a hydroxyl group and n is 0 or 1. Preferably there are employed amines of formula III wherein $R_1$, $R_2$, $R_3$ and $R_5$ are hydrogen, $R_8$ is hydrogen, or preferably a hydroxy group, $R_4$ is hydrogen or a methyl group and n is 0. Which amidoacid is best suited for which base in special cases can be cleared up through a preliminary experiment.

A great advantage of the process of the invention is that the pharmaceutically nonusable byproduct accumulating in the splitting of the racemate and also the antipode not changeable back into the original racemate by the racemization can be converted into the amidoacid I. Thereby with this otherwise worthless byproduct new racemate can be split.

The advantage of the process of the invention in the following will be explained in the industrially important racemate splitting of (±) norephedrine (NE). The pharmaceutically nonusable right rotating antipode (+)-norephedrine ((+)=NE; formula IV) is transposed in known manner (see above) into the (−)-ψ-norephedrine (formula V, (−)-ψ-NE)

$$\underset{VI\ (+)-NE}{\underset{}{\bigcirc}\!\!-\!\!\overset{OH}{\underset{|}{CH}}\!-\!\overset{CH_3}{\underset{|}{CH}}\!-\!NH_2} \longrightarrow \underset{V,\ (-)-\psi-NE}{\underset{}{\bigcirc}\!\!-\!\!\overset{CH_3}{\underset{|}{CH}}\!-\!\underset{\underset{OH}{|}}{CH}\!-\!NH_2}$$

By reacting with maleic anhydride there is recovered from this the corresponding amidoacid (formula VI, (+)-ω-NEMA) in high yield $$V + O = \underset{O}{C\diagdown\diagup}\overset{\overset{CH=CH}{|\quad\ \ |}}{C} = O \longrightarrow$$

$$\underset{VI,\ (+)-\psi-NEMA}{\underset{}{\bigcirc}\!\!-\!\!\underset{\underset{OH}{|}}{CH}\!-\!\overset{CH_3}{\underset{|}{CH}}\!-\!NH\!-\!\underset{\underset{O}{\|}}{C}\!-\!CH\!=\!CH\!-\!COOH}$$

Already in the stirring up of this acid with (±)-norephedrine in a solvent the more difficulty soluble (−)-NE salt of the (+)-ψ-NEMA precipitates out. Acid or alkaline splitting of the salt obtained yields (−)-norephedrine as well as the unchanged (+)-ψ-NEMA. The small (+)-ψ-NEMA loss is compensated in simple manner from the (+)-norephedrine likewise coming out of the mother liquor in the racemate splitting through the above described sequence of reaction.

In contrast in using the succinic acid or phthalic derivatives which are analogeous to formula VI the racemate splitting of (±) norephedrine proceeds only very unsatisfactorily. Yields and ability to crystallize of the diastereomeric salts are poor and besides the undesired (+)-NE-form precipitates out first as the more difficulty soluble component in the salt formation. It is unexpected that by changing from a saturated or aromatic dicarboxylic acid to an unsaturated dicarboxylic acid, the amidoacids produced from this and the worthless optical antipodes of an amine of formula III form diastereomeric salts of optically active bases which have the desired solubility and crystallization properties in optimal manner for a racemate splitting. Furthermore it is surprising that in salts of the amidoacids whose foundation bases have more than one asymmetrical center the solubility differences can be increased still further if before the production of the amidoacid there can be undertaken a configuration inversion at one of these centers (for example change of norephedrine into the corresponding pseudoform).

A further advantage is in the simple recovery of the added amidoacid after the splitting of the racemate.

Unless otherwise indicated all parts and percentages are by weight.

The process can comprise, consist essentially of the steps set forth with the materials described.

EXAMPLE 1

(−)-Norephedrine 250 grams of (±)-norephedrine were stirred with 206 grams of (+)-ψ-N-(1-methyl-2-phenyl-2-hydroxyethyl)-maleic acid monoamide (Abbreviation: (+)-ψ-NEMA) in 2.28 liters of methyl ethyl ketone for 6 hours at an interval temperature of 10°–120° C.

Then there was filtered off with suction the precipitated (+)-ψ-NEMA salt of the (−)-norephedrine.

After washing with acetone it was dried at 60° C. in a vacuum.

Yield: 309.8 grams=93.6% of theory;

M.P. 148°–150° C.

$[\alpha]_D^{20}$ (2.5% in 96% ethanol): −63.4°.

300 grams of this salt was suspended in 250 ml of water and treated with 68 ml of 45% aqueous sodium hydroxide. The mixture was shaken once with 450 ml of chloroform and six times with, in each case, 150 ml of chloroform. The combined chloroform extracts were dried with potassium carbonate and the solvent distilled off under reduced pressure. The residue was dissolved in 450 ml of toluene, after cooling innoculated with (±)-norephedrine base and placed in water for 12 hours at 10° C., whereby a small amount of unchanged (±)-norephedrine precipitated out (10.5 grams after drying).

The toluene filtrate was distilled off in a vacuum.

The residue crystallizing in the cooling off consisted of pure (−)-norephedrine.

Yield: 98.9 grams=87% of theory;

M.P. 49°–51° C.

$[\alpha]_D^{20}$ (5% in ethanol): −13.84°.

Recovery of the (+)-ψ-NEMA

The aqueous phase separated off in the extraction by shaking of the (−)-norephedrine was treated under cooling with 750 ml of water and 204 ml of concentrated hydrochloric acid. The mixture was cooled for several hours with water, filtered with suction, the precipitate washed with water and dried at 60° C. in a vacuum.

Yield: 176 grams −94% of theory

M.P. 149°–151° C.

$[\alpha]_D^{20}$ (2.5% in 96% ethanol): +17.2°.

(+)-Norephedrine

The acetone filtrate obtained in the splitting of the racemate of (±) norephedrine was acidified with concentrated sulfuric acid under cooling. The precipitated crude (+)-norephedrine sulfate was filtered off with suction and dried at 80° C.

Crude Yield: 168 grams.

156.5 grams of this sulfate were stirred up in 313 ml of water, made alkaline with 80 ml of 45% aqueous sodium hydroxide and shaken up six times with chloroform. After drying and distilling off of the combined extracts the product was dissolved in 470 ml of toluene, innoculated with (±)-norephedrine and allowed to stand for 12 hours at 10° C. The precipitated (±)-norephedrine base (24.6 grams) was filtered off with suction and the toluene distilled off under reduced pressure.

Yield: 95.2 grams=80.5% of theory

M.P. 48°–50° C.

$[\alpha]_D^{20}$ (5% in ethanol): 13.55°.

EXAMPLE 2

(−)-Norephedrine 10 grams of (±)-norephedrine were stirred together with 16.5 grams of (+)-N-(1-methyl-2-phenyl-2-hydroxyethyl)-maleic acid monoamide (Abbreviation: (+)-NEMA) in 160 ml of methyl isobutyl ketone at 50° C. for 6 hours. The mixture was allowed to stand at 50° C. overnight, filtered off with suction, washed with methyl isobutyl ketone and dried at 60° C. in a vacuum. Yield of (−)-norephedrine-(+)-NEMA salt's 9.7 grams=73% of theory; M.P. 156°-166° C.

The thus obtained 9.7 grams of the (−)-norephedrine salt were suspended in 75 ml of water, 2.2 ml of concentrated hydrochloric acid added and the mixture stirred a further 15 minutes. The precipitated (+)-NEMA was filtered off with suction, washed with water and dried at 60° C. Yield: 5.7 grams=94.6% of theory.

To isolate the (−)-norephedrine the aqueous filtrate was evaporated in a vacuum, the residue stirred with acetone and the crude hydrochloride filtered off with suction. By recrystallization from isopropanol there were obtained 3.3 grams of (−)-norephedrine hydrochloride. Yield 73.4% of theory;

M.P. 166°-171° C.

$[\alpha]_D^{20}$ (5% in water): −32.3°.

EXAMPLE 3

(+)-Phenylisopropylamine 40 grams of (±)-phenylisopropylamine and 36.9 grams of (+)-ψ-NEMA were stirred for 10 hours in 190 ml of acetone. The mixture was allowed to stand for a further 15 hours at 20° C. and the (+)-phenylisopropylamine salt of the (+)-ψ-NEMA which crystallized out was filtered off with suction.

Yield: 52.5 grams=92.2% of theory.

M.P. 150° C.

$[\alpha]_D^{20}$ (2.5% in ethanol): −48.0°.

50 grams of this salt together with 30 ml of water and 11.7 ml of concentrated hydrochloric acid were stirred for 30 minutes. The precipitated (+)-ψ-NEMA which precipitated was filtered off with suction and dried in a vacuum (35 grams=95.5% of theory). The aqueous filtrate was concentrated in a vacuum, made strongly alkaline with soda lye and the optically active amine separated off by shaking 5 times with chloroform. After distilling off the chloroform the residue was dissolved in dry ether and the (+)-phenylisopropylamine precipitated with isopropanolic hydrochloric acid. The mixture was allowed to stand for 2 to 3 days in the refrigerator and then the hydrochloride was filtered off with suction.

Yield: 17.2 grams=76.2% of the theory;

M.P. of the hydrochloride 149°-151° C.

$[\alpha]_D^{20}$ (5% in water: +24.2° (hydrochloride).

EXAMPLE 4

(+) and (−) α-Phenylethylamine 100 grams of racemic α-phenylethylamine and 102.8 grams of (−)-ψ-NEMA were stirred up in 1 liter of acetone for 7 hours at 20° C. The mixture was allowed to stand overnight, filtered off with suction and recrystallized from ethanol.

Yield: 113.9 grams of salt=74.5% of theory.

M.P. 149°-151° C.

$[\alpha]_D^{20}$ (2.5% in ethanol): +52.81°

63.3 grams of this salt were stirred up for 20 minutes with 390 ml of water and 14.5 ml of concentrated hydrochloric acid, allowed to stand for several hours at 10° C. and the (−)-ψ-NEMA filtered off with suction. (43 grams=98% of theory).

The aqueous filtrate was sharply concentrated, treated with 50 ml of 32% aqueous sodium hydroxide and shaken up four times with ether. The combined ether extracts were dried with KOH, the ether distilled off and the liquid residue distilled at 12 mn Hg. There was obtained the (+)-α-phenylethylamine in a yield of 19.9 grams (=93.2% of theory);

M.P. 68°-70° C.

$[\alpha]_D^{20}$ (5% in benzene): +40.9°.

To produce the (−)-α-phenylethylamine to acetone filtrate from the salt precipitation can be evaporated and the residue distilled. There is obtained the left rotating amine in a yield of 88%. The specific rotation is between 31° and 35°.

Optically purest (−)-α-phenylethylamine $[\alpha]_D^{20}$: −40° can be obtained through reaction of the (±) base with (+)-ψ-NEMA. Molar ratios, experimental conditions and yields are as described above in the production of (+)-α-phenylethylamine.

EXAMPLE 5

(+)- and (−)-p-Hydroxynorephedrine

A mixture of 100 grams of (±)-p-hydroxynorephedrine, 74.5 grams of (+)-ψ-NEMA and 1.05 liters of acetone were stirred for 20 hours at 20° to 23° C. and subsequently allowed to stand for 48 hours. The product was filtered off with suction and dried in a vacuum at 60° C.

Yield: 86.8 grams=69.7% of theory.

M.P. 98°-104° C.

$[\alpha]_D^{20}$ (5% in ethanol): −62.5°.

80 grams of this (+)-ψ-NEMA salt were stirred for a but 1 hour with 96 ml of 2 N NAOH at room temperature. The mixture was placed overnight in the refrigerator, filtered off with suction and washed with a little water and dried at 40° C. in a vacuum.

Yield: 23.7 grams=73.8% of theory.

For further purification the thus obtained (−)-p-hydroxynorephedrine can be recrystallized from isopropanol. M.P. 164°-167° C.

$[\alpha]_D^{20}$ (3.5% in 1 N HCl): −40.94°.

The (+)-p-hydroxynorephedrine can be obtained from the acetone mother liquor by addition of about 70 grams of (-ψ-NEMA and allowing to stand for several days (about 3 days), whereby the norephedrine compound precipitates out in the form of the (−)-ψ-NEMA salt. This salt can then be split up in the usual way.

If there is employed (±)-p-hydroxynorephedrine initially with (−)-ψ-NEMA then there is obtained the pure+form directly.

EXAMPLE 6

(+)- and (−)-p-Hydroxynorephedrine

A mixture of 100 grams of (±)-p-hydroxynorephedrine, 149 grams of (−)-NEMA and 1.25 liters of absolute ethyl alcohol were stirred for 8 hours at 20° C. and allowed to stand for a further 16 hours. The (−)-NEMA salt of (−)-p-hydroxynorephedrine which crystallized out was filtered with suction and for purification was boild with 550 ml of isopropanol. After cooling it was filtered off with suction and dried in a vacuum at 60° C.

Yield: 94.3 grams=75.7% of theory.
M.P. 163°–165° C.
$[\alpha]_D^{20}$ (1% in absolute ethanol): +4.1°.

Recovery of the (−) Base

The free base was recovered from this salt in a manner analogous to Example 5.
Yield 72.0%,
M.P. 162°–166° C.
$[\alpha]_D^{20}$ (2% in absolute ethanol): −17.5°
$[\alpha]_D^{20}$ (3.5% in 1 N NCl): −40.7°

Recovery of the (+) Base

The ethanolic filtrate from the splitting of the racemate was evaporated in a vacuum and the residue recrystallized from isopropanol. There were obtained 127.5 grams of crude (−)-NEMA salt of (+)-p-hydroxynorephedrine. By stirring with 152 ml of 2 N NaOH and subsequent standing for 12 hours in the refrigerator the (+) base separated out therefrom. The product was filtered off with suction and recrystallized from isopropanol.
Yield: 60.4% M.P. 163°–166° C.
$[\alpha]_D^{20}$ (2% in absolute ethanol): +17.35°.

What is claimed is

1. A process for preparing an optically active base from a racemic base

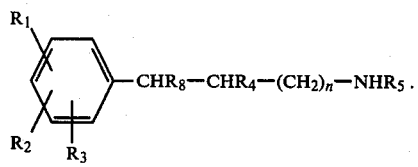

comprising reacting the racemic base in a solvent with an optically active half amide of an unsaturated aliphatic dicarboxylic acid of the formula

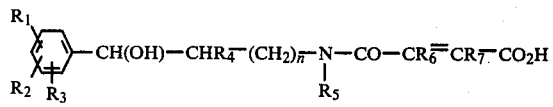

where $R_1$, $R_2$ and $R_3$ are hydrogen, halogen, a hydroxy group, a methyl group or a methoxy group or two of $R_1$, $R_2$ and $R_3$ together are a methylenedioxy group, $R_4$ is a methyl group, $R_5$, $R_6$ and $R_7$ are hydrogen or a $C_1$–$C_4$ alkyl group, $R_8$ is hydrogen or a hydroxy group and n is 0 or 1.

2. A process according to claim 1 also including the step of splitting an optically active homogeneous salt fraction into the corresponding optically active base and the added half amide.

3. A process according to claim 2 wherein the splitting is carried out with a strong acid or a base.

4. A process according to claim 1 wherein $R_5$ is hydrogen, one of $R_6$ and $R_7$ is hydrogen and the other of $R_6$ and $R_7$ is hydrogen or methyl.

5. A process according to claim 1 wherein the solvent comprises an alcohol, ketone, ester, amide, ether or water.

6. A process according to claim 1 wherein the temperature is 0°–100° C.

7. A process according to claim 1 wherein in the racemic base $R_1$ is hydrogen, $R_2$ is hydrogen and $R_3$ is a hydroxy group or hydrogen and $R_5$ is hydrogen or methyl.

8. A process according to claim 7 wherein in the racemic base $R_1$, $R_2$, $R_3$ and $R_5$ are hydrogen, $R_8$ is hydrogen or a hydroxy group $R_4$ is methyl and n is 0.

9. A process according to claim 7 wherein in the racemic base $R_1$, $R_2$, $R_3$ and $R_5$ are hydrogen, $R_8$ is a hydroxy group, $R_4$ is methyl and n is 0.

10. A process according to claim 1 wherein the halfamide has the formula

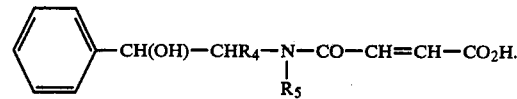

11. A process according to claim 10 wherein the solvent comprises an alcohol, ketone, ester, amide, ether or water.

12. A process according to claim 10 wherein the temperature is 0°–100° C.

13. A process according to claim 10 wherein in the racemic base $R_1$ is hydrogen, $R_2$ is hydrogen and $R_3$ is a hydroxy group or hydrogen and $R_5$ is hydrogen or methyl.

14. A process according to claim 13 wherein in the racemic base $R_1$, $R_2$, $R_3$ and $R_5$ are hydrogen, $R_8$ is hydrogen or a hydroxy group, $R_4$ is methyl and n is 0.

15. A process according to claim 13 wherein in the racemic base $R_1$, $R_2$, $R_3$ and $R_5$ are hydrogen or methyl and n is 0.

16. A process according to claim 10 wherein in the formula $R_5$ is hydrogen.

17. A process according to claim 16 wherein in the racemic base $R_1$ is hydrogen, $R_2$ is hydrogen and $R_3$ is a hydroxy group or hydrogen and $R_5$ is hydrogen or methyl.

18. A process according to claim 17 wherein in the racemic base $R_1$, $R_2$, $R_3$ and $R_5$ are hydrogen, $R_8$ is hydrogen or a hydroxy group, $R_4$ is methyl and n is 0.

19. A process according to claim 17 wherein in the racemic base $R_1$, $R_2$, $R_3$ and $R_5$ are hydrogen, $R_8$ is a hydroxy group, $R_4$ is methyl and n is 0.

20. A process according to claim 10 wherein $R_4$ is methyl and $R_5$ is hydrogen.

21. A process according to claim 20 wherein in the racemic base $R_1$ is hydrogen, $R_2$ is hydrogen and $R_3$ is a hydroxy group or hydrogen and $R_5$ is hydrogen or methyl.

22. A process according to claim 20 wherein in the racemic base $R_1$, $R_2$, $R_3$ and $R_5$ are hydrogen, $R_8$ is hydrogen or a hydroxy group, $R_4$ is methyl and n is 0.

23. A process according to claim 20 wherein in the racemic base $R_1$, $R_2$, $R_3$ and $R_5$ are hydrogen, $R_8$ is a hydroxy group, $R_4$ is methyl and n is 0.

24. A process according to claim 10 wherein the maleic acid halfamide is that of (+)-pseudonorephedrine or of (−)-pseudonorephedrine.

25. A process according to claim 24 wherein is the racemic base $R_1$ is hydrogen, $R_2$ is hydrogen and $R_3$ is a hydroxy group or hydrogen and $R_5$ is hydrogen or methyl.

26. A process according to claim 25 wherein in the racemic base $R_1$, $R_2$, $R_3$ and $R_5$ are hydrogen, $R_8$ is hydrogen or a hydroxy group, $R_4$ is methyl and n is 0.

27. A process according to claim 25 wherein in the racemic base $R_1$, $R_2$, $R_3$ and $R_5$ are hydrogen, $R_8$ is a hydroxy group, $R_4$ is methyl and n is 0.

* * * * *